US009309575B2

(12) United States Patent
Koprowski et al.

(10) Patent No.: US 9,309,575 B2
(45) Date of Patent: Apr. 12, 2016

(54) **MUTANT STRAINS OF *ESCHERICHIA COLI*, A METHOD OF TESTING POTENTIAL ANTIBACTERIAL AGENTS USING SAID STRAINS AS WELL AS A TESTING KIT**

(75) Inventors: Piotr Koprowski, Warsaw (PL); Andrzej Kubalski, Warsaw (PL); Wojciech Grajkowski, Warsaw (PL)

(73) Assignee: Instytut Biologii Doswiadczalnej IM. M. Nenckiego Pan, Warszawa (PL)

( * ) Notice: Subject to any disclaimer, the term of this patent is extended or adjusted under 35 U.S.C. 154(b) by 406 days.

(21) Appl. No.: 13/642,121

(22) PCT Filed: Apr. 23, 2011

(86) PCT No.: PCT/PL2011/050010
§ 371 (c)(1),
(2), (4) Date: Oct. 18, 2012

(87) PCT Pub. No.: WO2011/133056
PCT Pub. Date: Oct. 27, 2011

(65) Prior Publication Data
US 2013/0040336 A1 Feb. 14, 2013

(30) Foreign Application Priority Data
Apr. 23, 2010 (PL) .......................... 391045

(51) Int. Cl.
| C12N 1/21 | (2006.01) |
| C12Q 1/18 | (2006.01) |
| C12R 1/19 | (2006.01) |
| C07K 14/245 | (2006.01) |
| C12N 1/20 | (2006.01) |

(52) U.S. Cl.
CPC ............ *C12R 1/19* (2013.01); *C07K 14/245* (2013.01); *C12N 1/20* (2013.01); *C12Q 1/18* (2013.01)

(58) Field of Classification Search
CPC ........... C12Q 1/18; C12N 1/20; C07K 14/245
See application file for complete search history.

(56) References Cited

U.S. PATENT DOCUMENTS

| 6,537,778 | B1 | 3/2003 | Zuker |
| 6,942,979 | B1 | 9/2005 | Honore |
| 7,396,816 | B2 | 7/2008 | Yokotagawa |
| 7,429,449 | B2 | 9/2008 | Leberer |
| 2003/0049697 | A1 | 3/2003 | Lazdunski |
| 2003/0073117 | A1 | 4/2003 | Suzuki |
| 2006/0024729 | A1 | 2/2006 | Honore |
| 2009/0162368 | A1 | 6/2009 | Honore |

FOREIGN PATENT DOCUMENTS

| EP | 1260585 | 11/2002 |
| EP | 1535903 | 6/2005 |
| WO | 2005/002521 | 1/2005 |
| WO | 2005/051902 | 6/2005 |
| WO | 2005/070122 | 8/2005 |
| WO | 2009031818 | 3/2009 |

OTHER PUBLICATIONS

Stumpe, S., et al. 1996 Handbook of Biological Physics vol. 2 chapter 21: 473-499.*
Corry, Ben and Martinac, Boris, "Bacterial mechanosensitive channels: experiment and theory", Biochim Biophys Acta, 1778(9):1859-1870 (2008).
Datsenko, Kirill A. and Wanner, Barry L., "One-step inactivation of chromosomal genes in *Escherichia coli* K-12 using PCR products", Proc Natl Acad Sci USA, 97(12):6640-6645 (2000).
Dixon, Ronald A. and Chopra, Ian, "Leakage of periplasmic proteins from *Escherichia coli* mediated by polymyxin B nonapeptide", Antimicrob Agents Chemother, 29(5):781-788 (1986).
Edwards, Michelle D. et al., "Pivotal role of the glycine-rich TM3 helix in gating the MscS mechanosensitive channel", Nat Struct Mol Biol, 12(2):113-119 (2005).
Hamill, Owen P. and Martinac, Boris, "Molecular basis of mechanotransduction in living cells", Physiol Rev, 81(2):685-740 (2001).
Kloda, Anna et al., "Mechanosensitive channel of large conductance", Int J Biochem Cell Biol, 40(2):164-169 (2007).
Koprowski, Piotr et al., "Bacterial ion channels as the model structures", Kosmos, 269 54(4):373-379 (article in Polish with summary in English) (2005).
Koprowski, Piotr et al., "Genetic screen for potassium leaky small mechanosensitive channels (MscS) in *Escherichia coli*: recognition of cytoplasmic β domain as a new gating element", J Biol Chem, 286(1):877-888 (2010).
Li, Chan et al., "Identification of mutations that alter the gating of the *Escherichia coli* mechanosensitive channel protein MscK", Mol Microbiol, 64(2):560-574 (2007).
Ou, Xiaorong et al., "One face of a transmembrane helix is crucial in mechanosensitive channel gating", Proc Natl Acad Sci U S A, 95(19)11471-11475 (1998).

(Continued)

*Primary Examiner* — Marsha Tsay
(74) *Attorney, Agent, or Firm* — Rodney J. Fuller; Booth Udall Fuller, PLC

(57) ABSTRACT

The subject of the present invention are mutant strains of *Escherichia coli* MG6165 (ATCC nr 47076) lacking all potassium transporters: Kdp, Kup and Trk (ΔKtrans), encompassing strains lacking at least one of the genes encoding mechanically gated channels mscS and mscL (ΔKtrans ΔmscS i/lub ΔmscL). In particular, it concerns *Escherichia coli* MG61655 (ATCC No. 47076) lacking all potassium transporters: Kdp, Kup and Trk (ΔKtrans), which additionally are devoid of the mechanically gated channel gene mscS—*E. coli* (ΔKtrans ΔmscS), the mechanically gated channel gene mscL—*E. coli* (ΔKtrans ΔmscL) and/or both the mechanically gated channel genes mscS and mscL—*E. coli* (ΔKtrans ΔmscS ΔmscL). The subject of the present invention is also a method of testing chemical compounds for potential antibacterial properties, making use of the abovementioned strains. Another subject of the present invention is a kit for testing chemical compounds as potential antibacterial substances, containing the abovementioned strains.

8 Claims, No Drawings

(56) References Cited

OTHER PUBLICATIONS

Parfenova, Lyubov V. et al., "Modulation of MthK potassium channel activity at the intracellular entrance to the pore", J Biol Chem, 281(30):21131-21138 (2006).

Uozumi, Nobuyuki, *Escherichia coli* as an expression system for K(+) transport systems from plants", Am J Physiol Cell Physiol, 281(3):C733-C739 (2001).

Vaara, M. and Viljanen, P., "Binding of polymyxin B nonapeptide to gram-negative bacteria", Antimicrob Agents Chemother, 27(4):548-554 (1985).

Viljanen, P. and Vaara, M., "Susceptibility of gram-negative bacteria to polymyxin B nonapeptide", Antimicrob Agents Chemother, 25(6):701-705 (1984).

ISR of PCT/PL2011/050010 mailed Sep. 9, 2011.

* cited by examiner

SEQUENCE LISTING

<160> NUMBER OF SEQ ID NOS: 10

<210> SEQ ID NO 1
<211> LENGTH: 50
<212> TYPE: DNA
<213> ORGANISM: Artificial Sequence
<220> FEATURE:
<223> OTHER INFORMATION: primer trkA H1

<400> SEQUENCE: 1
taataaggcg tcattagacg ccttattaat tacaagaaga aagggcttgg          50

<210> SEQ ID NO 2
<211> LENGTH: 50
<212> TYPE: DNA
<213> ORGANISM: Artificial Sequence
<220> FEATURE:
<223> OTHER INFORMATION: primer trkA H2

<400> SEQUENCE: 2
tttacgctaa gctaatcaaa aagtgatgag ataacgggtc gcgactgatg          50

<210> SEQ ID NO 3
<211> LENGTH: 50
<212> TYPE: DNA
<213> ORGANISM: Artificial Sequence
<220> FEATURE:
<223> OTHER INFORMATION: primer kdpABC H1

<400> SEQUENCE: 3
gactcatatt cagtgctcac tcaatatcat caggagagat attccgccac          50

<210> SEQ ID NO 4
<211> LENGTH: 50
<212> TYPE: DNA
<213> ORGANISM: Artificial Sequence
<220> FEATURE:
<223> OTHER INFORMATION: primer kdpABC H2

<400> SEQUENCE: 4
gtcattgatt tactgctgac cgtttgcggt ctggtgtgag gtttaccatg          50

<210> SEQ ID NO 5
<211> LENGTH: 50
<212> TYPE: DNA
<213> ORGANISM: Artificial Sequence
<220> FEATURE:
<223> OTHER INFORMATION: primer kup H1

<400> SEQUENCE: 5
ccccttatga agaaaggagg cgtctggcgt tagatttcga cctgagtacc          50

<210> SEQ ID NO 6
<211> LENGTH: 50
<212> TYPE: DNA
<213> ORGANISM: Artificial Sequence
<220> FEATURE:
<223> OTHER INFORMATION: primer kup H2

<400> SEQUENCE: 6
gccaagggac taagcacaca tttcatattt caacgaaaga ctagtctatg          50

<210> SEQ ID NO 7
<211> LENGTH: 50
<212> TYPE: DNA
<213> ORGANISM: Artificial Sequence

```
<220> FEATURE:
<223> OTHER INFORMATION: primer mscS H1

<400> SEQUENCE: 7
cagagagtat tatctggcct cagcgttgat tacgcagctt tgtcttcttt            50

<210> SEQ ID NO 8
<211> LENGTH: 50
<212> TYPE: DNA
<213> ORGANISM: Artificial Sequence
<220> FEATURE:
<223> OTHER INFORMATION: primer mscS H2

<400> SEQUENCE: 8
ggcggagtgt atttctccat tttgagtcag ttgaaaagga atattgaatg            50

<210> SEQ ID NO 9
<211> LENGTH: 50
<212> TYPE: DNA
<213> ORGANISM: Artificial Sequence
<220> FEATURE:
<223> OTHER INFORMATION: primer mscL H1

<400> SEQUENCE: 9
accactggtc ttctgctttc aggcgcttgt taagagcggt tattctgctc            50

<210> SEQ ID NO 10
<211> LENGTH: 50
<212> TYPE: DNA
<213> ORGANISM: Artificial Sequence
<220> FEATURE:
<223> OTHER INFORMATION: primer mscL H2

<400> SEQUENCE: 10
ttaacatttg ttagacttat ggttgtcggc ttcataggga gaataacatg            50
```

MUTANT STRAINS OF *ESCHERICHIA COLI*, A METHOD OF TESTING POTENTIAL ANTIBACTERIAL AGENTS USING SAID STRAINS AS WELL AS A TESTING KIT

RELATED APPLICATION DATA

This application is the U.S. National Stage of International Application No. PCT/PL2011/050010, filed Apr. 23, 2011, which claims the benefit of Polish Application No. P.391045, filed Apr. 23, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,155 byte ASCII (text) file named "Seq_List" created on Oct. 18, 2012.

The subject of the present invention are mutated strains of *Escherichia coli*, a method and kit for testing potential antibacterial agents that are activators of bacterial mechanoreceptive channels which make use of the mutated strains.

Ion channels are specialised membrane proteins that facilitate the flow of ions across a cell membrane along to a concentration gradient. In their closed state, channels do not conduct ions, and they may open under the influence of an altered membrane electrical potential (voltage-gated channels), ligands, or mechanical tension of the membrane (mechanoreceptive channels). During opening, a channel element referred to as the gate changes its position and uncovers the pore of the channel, enabling ion flow. Channel opening times are very short (several milliseconds), and ion movement occurs at a rate in the neighbourhood of $10^6$ ions/s. Ion channels may conduct particular ions, and are then referred to as having selectivity filters. Depending on the type of ion conducted, we can distinguish cationic and anionic channels, and among the former: potassium, sodium and calcium channels. Ion flux through a channel occurs along the concentration gradient on both sides of the cell membrane.

Mechanically gated channels (MG) are activated by the mechanical tensioning of the cell membrane and their existence has been observed in animal, plant and bacterial cells. MG channels, in addition to electrically gated and ligand-modulated ion channels constitute the third major ion channel class. MG channels are detectors of all manner of mechanical stimuli that play a role in touch, hearing, and equilibrium maintenance. They may react to membrane tension caused by forces generated by a cell itself during fission, morphogenesis and growth, and they may constitute a universal protective mechanism in all cells against osmotic shock (sudden shifts in environmental osmolarity) and it is this property that seems to explain their occurrence in bacteria (Hamill O. P., Martinac B., 2001, *Molecular basis of mechanotransduction in living cells*. Physiol. Rev. 81, 685-740). Two bacterial MG channels from the plasmalemma of *Escherichia coli*: MscS (low conductivity MG channel) and MscL (high-conductivity MG channel) are, thus far, the best studied mechanoreceptive proteins, both in terms of structure and function. Bacterial MG channels are characterised by high conductivity and large tension values that gate them. These are characteristics that differ them from eukaryotic MG channels. The conductivity of the MscL channel is some 100-fold that of the medium eukaryotic channel (MscS conductivity is about 30-fold) (Koprowski P., Grajkowski W., Kubalski A., *Bakteryjne kanaty jonowe jako struktury modelowe*., Kosmos, 2005, tom 54, No. 4 (269) str. 373-379).

Most bacteria, including pathogenic ones, occur in osmotically stochastic environments (i.e. human organism—water). During hypotonic shock (transfer from high osmolarity into low osmolarity) bacterial membranes are subjected to considerable osmotic pressure, which may lead to disruption of the cell. It has been demonstrated that the mechanically gated channels MscS and MscL, which are opened by cell membrane tension are necessary for the survival of osmotic shock by bacteria. *Escherichia coli* cells devoid of the active products of the mscS and mscL genes and subjected to osmotic shock undergo lysis. In accordance with the essential role of the mechanically gated channels MscS and MscL in bacteria, the genes of these proteins are found in all sequenced bacterial genomes. These channels constitute a pathway for "ejecting" excess osmoliths and water from the cell in a short time. Thus they are channels of the highest conductivity. The regulation of their activity is of key significance in cell survival. Uncontrolled opening results in the de-energization and death of cells. A series of mutants of MscL and MscS channels have been discovered, whose expression is toxic to cells (gain-of-function phenotype). Such a phenotype is possible due to the relatively extensive ion flux in conditions under which a wild-type channel remains closed. A greatly reduced gating threshold has been observed in the mutant channels.

U.S. Pat. No. 6,537,778 B1 discloses nucleic acids encoding an eukaryotic mechanically gated protein (Msc), methods of isolating modulators (meaning activators, inhibitors, enhancers, etc.) of mechanically gated conducting channels using isolated, naturally occurring or recombinant Msc proteins or fragments thereof using in vitro and in vivo binding assays known from the art and kits for isolating Msc protein modulators containing appropriate reagents and instructions.

U.S. Pat. No. 6,942,979 B1, US 2003/0049697 A1, U.S. Pat. No. 7,468,422 B2, US 2006/0024729 A1 and US 2009/0162368 A1 disclose a purified protein encompassing a mechanically gated potassium channel and at least one polyunsaturated fatty acid, as well as rilusol, the use of such channels in the identification of potential drugs as well as methods of identifying substances capable of modulating the potassium flux through the potassium channel TRAAK treated with arachidonic acid.

Patent description U.S. Pat. No. 7,429,449 B2 discloses methods of identifying inhibitors and activators of eukaryotic potassium channels using *Saccharomyces cerevisiae* cells, which do not express the functional endogenous potassium channels TRK1, TRK2 and TOK1, but which express heterologous, eukaryotic potassium channels as well as methods of manufacturing and uses of such mutant cells.

Patent description US 2003/0073117 A1 discloses novel mechanically gated channel proteins obtained from mice and humans (SAC1 and hSAC respectively), which are specifically expressed in the kidney and play a role in the non-selective transport of cations into cells in response to an appropriate mechanical stimulus, DNA encoding such cells, a method of identifying activators and inhibitors of the cation channel activity using these proteins as well as an antibody against these proteins.

European patent description EP 1 535 903 A1 and the international patent application WO 2005/051902 A2 disclose compounds and methods used in the chemical modification of the protein channel for use in pharmaceutical carriers for the controlled and/or local release of therapeutic molecules (i.e. small molecules, peptides, proteins and other macromolecules), as well as compounds sensitive to pH and/ or light capable of modifying a mechanically gated channel such as the MscL protein of *E. coli* or its functional equivalent, the use of these compounds in the transformation of a mechanically gated channel into a pH and/or photo gated channel as well as the use of such altered channels in the production of drugs.

Patent description U.S. Pat. No. 7,396,816 B2 discloses novel polypeptides which specifically inhibit the activity of a mechanically gated channel as well as inhibitors of the mechanically gated channel and drugs against atrial fibrillation containing such polypeptided and their salts.

Patent description WO 2005/002521 A2 describes, amongst others, methods for identifying compounds which inhibit the expression of a gene of a potassium-transporting protein or the biological activity of this gene which encompass testing ligand binding, testing protein activity, cell assays and assays for the expression of TRK gene expression.

International application WO 2005/070122 discloses methods of identifying agents which decrease the activity of mechanically gated ion channels, preferentially a $Ca^{2+}$ permeable channel (MscCa), as well as methods using agents that decrease the activity of mechanically gated ion channels, which encompass for example methods of treating cancer, methods of decreasing metastases and methods of reducing cancer symptoms Recently, a different method has been used to isolate mutants of MscS channel A strain of *E. coli*, LB2003 (trkA kup1 (trkD1) kdpABC5 rpsL metE thi rha gal), lacking potassium transporters, requires a high concentration of potassium ions in the medium for optimal groth (>30 mM $K^+$). A strain possessing potassium transporters can grow in submilimolar concentrations of $K^+$ ions. The expression in LB2003 of proteins constituting alternate pathways of $K^+$ ion transport (i.e. membrane channels which open due to a particular stimulus and facilitate the influx/efflux of $K^+$ from and into the cell) facilitates the restitution of cell growth in low-potassium media. This strategy has been used in the past in the isolation of genes encoding potassium channels. Mutants have been isolated that contain a series of mutations in the transmembrane domain of MscS, which has previously been identified as the channel gate. Furthermore, it turned out that the over-expression of a number of these mutants in a wild type strain inhibits cell growth. This phenotype is caused by a decreased channel opening threshold and the de-energization of the cells (gain-of-function phenotype).

Chemical compounds that open mechanically gated channels will mimic such mutations and will also lead to cell death. Such compounds with bacteriostatic or bacteriocidal properties will be of potential pharmacological use.

The subject of the present invention are mutated strains of *Escherichia coli* MG61655 (ATCC No. 47076), lacking all potassium transporters, meaning Kdp, Kup and Trk (ΔKtrans), including strains lacking at least one among of the mechanically gated channel genes mscS and mscL (ΔKtrans ΔmscS and/or ΔmscL). In particular, the present invention relates to *Escherichia coli* strains MG61655 (ATCC No. 47076) lacking all potassium transporters, meaning Kdp, Kup and Trk (ΔKtrans), which have further been devoided of the mechanically gated channel gene mscS (ΔKtrans ΔmscS), or the mechanically gated channel gene mscL (ΔKtrans ΔmscL) or both mechanically gated channel genes mscS and mscL (ΔKtrans ΔmscS ΔmscL).

The subject of the present invention is also a method of testing chemical compounds for particular antibacterial properties, which makes use of the abovementioned mutant strains, in which:

during the first stage of selection, the growth of mutant cultures of *E. coli* (ΔKtrans) lacking all potassium transporters, in the presence of a tested substance and various concentrations, including limiting concentrations of potassium, wherein the growth of the strain under such conditions indicates the facilitation of potassium transport into the cell by the examined substance, preferentially, during the second stage of selection, cell growth is measured in a culture of *E. coli* (ΔKtrans) mutants lacking all potassium transporters and a culture of mutants lacking all potassium transporters and both genes encoding mechanically gated channels, mscS and mscL, meaning *E. coli* (ΔKtrans ΔmscS ΔmscL), in the presence of a compound selected during stage one, at various concentrations, wherein the growth of both strains indicates that the tested substance is not active with regard to the MscS and MscL channel proteins, whereas the growth of the *E. coli* (ΔKtrans) in strain and the concurrent non-growth of *E. coli* (ΔKtrans ΔmscS ΔmscL) means that the examined substance is active against mechanically gated channels, preferentially, during the third stage of selection, the growth of a culture of *E. coli* (ΔKtrans ΔmscL) mutants is measured in the presence of a compound selected during the second stage (one which demonstrates an effect on mechanically gated channels) at various concentrations and limiting potassium concentrations, and cell growth demonstrates that this compound is a specific MscS channel activator, preferentially, during the fourth stage of selection, the growth of a culture of *E. coli* (ΔKtrans ΔmscS) mutants is measured in the presence of a compound selected during the second stage (demonstrating its effect on the activity of mechanically gated channels) at various concentrations and at limiting concentrations of potassium, wherein the growth of the of the culture indicates that the tested compound is a specific activator of the MscL channel.

The subject of the present invention is also a kit for testing chemical compounds as potential antibacterial substances, which contains the mutant strains mentioned above.

Production of the mutant strains of *Escherichia coli*, MG61655 (ATCC No. 47076)

All deletions are made using a standard method (Datsenko and Wanner, 2000). The following procedure facilitates the generation of multiple deletions. In this method, the cassette bearing kanamycine resistance and flanked with FRT sequences recognised by the FLP recombinase, a part of plasmid pKD13, is used as a template for PCR. The primers used in this reaction contain the P regions complementary to the template at their 3'-ends and H regions, complementary to the gene flanking sequence subject to deletion at their 5' ends. Next, the PCR products are transformed into *E. coli* cells expressing the λ, RED recombinase of the pKD46 plasmid which facilitates the homologous recombination of the transforming PCR products. The cells are then cultured at 37° C. on a selection medium containing kanamycin in order to isolate integrants of the kanamycin resistance gene. The isolated clones are cultured without antibiotics at 43° C. in order to eliminate plasmid pKD46. Next, the cells are transformed with plasmid pCP20 which expresses the FLP recombinase, which facilitates the excision of the kanamycin resistance gene from the genome. The transformants are selected at 30° C. on ampicillin, whereafter they are passaged non-selectively at 43° C. In this fashion, the plasmid pCP20 is eliminated from the cells. The bacteria are then tested for the loss of the antibiotic markers. Deletions are confirmed using PCR and the primers k1 5'-CGGCCACAGTCGATGAATCC-3' and k2 5'-CGGTGCCCTGAATGAACTGC-3'.

Datsenko K A, Wanner B L (2000.) One-step inactivation of chromosomal genes in Escherichia coli K-12 using PCR products. Proc Natl Acad Sci USA 97: 6640-6645.

Li, C., Edwards, M. D., Jeong, H., Roth, J., and I. R. Booth. 2007. Identification of mutations that alter the gating of the Escherichia coli mechanosensitive channel protein, MscK. Mol. Microbiol. 64:560-574.

Method of Testing Potential Antibacterial Compounds

The strain of E. coli (ΔKtrans), lacking potassium transporters, requires a high concentration of potassium ions (>30 mM $K^+$) in the medium for full growth, whereas a strain possessing the transporters can grow on submilimolar concentrations of $K^+$). The expression, in E. coli ΔKtrans, of proteins constituting alternate $K^+$ transport pathways (i.e. membrane channels that open due to a particular stimulus and facilitate the influx/efflux of $K^+$ to and from the cell), makes it possible to re-establish cell growth on media with low potassium concentrations (1-5 mM $K^+$). Mechanically gated channels with mutations in the channel gate (leaking) also enable $K^+$ flux at low potassium concentrations. Over-expression of a number of these mutants in a wild-type strain inhibits cell growth. This phenotype is caused by the decreased channel opening threshold and the deenergization of the cell (gain-of-function, phenotype, GOF).

Assay Using the Mutant E. coli (ΔKtrans ΔmscS ΔmscL)—Initial Selection Step of Compounds in Terms of Perforation of Mechanically Gated Channels The assays encompass the measurement of the growth of mutant strains of E. coli (ΔKtrans) in the presence of several concentrations of tested small molecule compounds (concentrations in the nanomolar to micromolar range). The growth of the strain in limiting potassium concentrations is evidence of the facilitation of potassium influx into the cell in the presence of the tested compound. E. coli (ΔKtrans) as well as E. coli (ΔKtrans ΔmscS ΔmscL) grow on high-$K^+$ media. If the addition of a compound from the pool of compounds evaluated for possible antibacterial activity causes a decrease in the minimum potassium concentration necessary for the growth of both strains, this means that the substance does not act upon the channel proteins MscS and MscL, but alters the properties of the membrane and/or membrane proteins other than mechanically gated channels, causing it to leak. On the other hand, the growth of E. coli (ΔKtrans) and non-growth of E. coli (ΔKtrans ΔmscL ΔmscS) in the presence of the examined compound indicates an effect on mechanically gated channel activity. This effect may be direct (through binding to the protein) or indirect (by incorporation into the plasmalemma and the modification of its properties). The differentiation between these scenarios is performed using the presence of limiting concentrations of potassium and of the tested compound, and both strains: E. coli (ΔKtrans ΔmscL) and E. coli (ΔKtrans.ΔmscS). In this case, the growth of both strains in the presence of the tested substance is evidence of the non-specific activity of the compound on mechanically gated channels (the MscS and MscL proteins exhibit no amino-acid nor structural similarity). On the other hand, the growth of one of the two strains identifies the compound as a specific activator of one of the channels.

Assay Using the Mutant E. coli (ΔKtrans ΔmscL).

The tested substance, identified previously as enabling the growth of strain E. coli (ΔKtrans), but not E. coli (ΔKtrans ΔmscS ΔmscL), is tested on E. coli (ΔKtrans ΔmscL). If the tested substance facilitates the growth of the strain E. coli (ΔKtrans ΔmscL) in low concentrations of potassium ions, this means that it is a specific activator of the MscS channel. The use of such a substance at a higher concentration than in the assays described above can lead to cell death. The effect will be achieved by the permeability of the closed MscS channel and is comparable to a mutation in various regions of the channel, i.e. the GOF mutation A98S in the gate which lowers the threshold of activation of the channel (Edwards et al., 2005).

Assays Using the Mutant E. coli (ΔKtrans ΔmscS).

The tested substance, identified previously as enabling the growth of strain E. coli (ΔKtrans), but not E. coli (ΔKtrans ΔmscS ΔmscL), is tested on E. coli (ΔKtrans ΔmscS). If the tested substance facilitates the growth of the strain E. coli (ΔKtrans ΔmscS) in low concentrations of potassium ions, this means that it is a specific activator of the MscL channel. The use of such a substance at a higher concentration than in the assays described above can lead to cell death. The effect will be achieved by the permeability of the closed MscL channel and is comparable to a mutation in various regions of the channel, i.e. the GOF mutation V23A in the gate region which lowers the activation threshold of the channel (Ou et al., 1998).

The above assays can be performed in the presence in media containing the polymyxin B nonapeptide (PMBN) at a concentration of 1-10 μg/ml. PMBN is a derivative of polymyxin B that does not exhibit biocidal properties at concentrations of 1-10 μg/ml, but which permeabilise the external membrane (1-3).

1) Susceptibility of gram-negative bacteria to polymyxin B nonapeptide (1984) Viljanen P, Vaara M. Antimicrob Agents Chemother. 25(6):701-5
2) Binding of polymyxin B nonapeptide to gram-negative bacteria (1985) Vaara M, Viljanen P. Antimicrob Agents Chemother. 27(4):548-54
3) Leakage of periplasmic proteins from Escherichia coli mediated by polymyxin B nonapeptide (1986) Dixon R A, Chopra I. Antimicrob Agents Chemother. 1986 May; 29(5):781-8
4) Edwards M D, Li Y, Kim S, Miller S, Bartlett W, Black S, Dennison S, Iscla I, Blount P, Bowie J U, Booth I R. (2005) Pivotal role of the glycine-rich TM3 helix in gating the MscS mechanosensitive channel Nat Struct Mol Biol. 12(2):113-9.
5) Ou X, Blount P, Hoffman R J, Kung C. (1998) One face of a transmembrane helix is crucial in mechanosensitive channel gating. Proc Natl Acad Sci USA.95(19):11471-5.

The following examples better illustrate the nature of the present invention.

EXAMPLE 1

Production of Mutants

Materials and Methods:

KLM medium: 10 g/l bacto tryptone (DIFCO), 5 g/l yeast extract (DIFCO), 10 g/l KCl, pH=7.0. The non-limiting medium for the growth of E. coli (ΔKtrans) mutants was $K_{115}$ containing $K_2HPO_4$, 46 mM; $KH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (Li et al., 2007). In order to obtain potassium-free medium, $K_0$, we used $Na_2HPO_4$, 46 mM; $NaH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (mass/volume). In order to prepare a medium with a medium potassium content, we mixed $K_{115}$ and $K_0$ media in appropriate proportions.

Strains lacking the activities of the three potassium transporters Kdp, Kup and Trk, have been described in literature numerous times.

In order to inactivate all potassium transporters, meaning Kdp, Kup and Trk we performed sequential deletions of genes for subunits of the transporters kdpABC, kup and trkA. The resulting strain, E. coli (ΔKtrans), was used for the deletion of mechanically gated channel genes mscS and mscL in order to obtain strains with the following genotypes: E. coli (ΔKtrans ΔmscL), E. coli (ΔKtrans ΔmscS) and E. coli (ΔKtrans ΔmscL ΔmscS).

For this reason we used primers 1 and 2 for the PCR amplification (using Pfu polymerase (Stratagene) in the manufacturer's buffer and recommended conditions) of the kanR cassette of the plasmid pKD13 (Datsenko and Wanner, 2000). Each of the primer pairs 1 and 2 consisted of two fragments, H and P, with the following structure 5'-$H_xP_x$-3'. Therefore, primer 1 had the structure 5'-$H_1P_1$-3'.

```
The P fragments were constant, and had the
following sequences:
P1:
5'-ATTCCGGGGATCCGTCGACC-3'
and

P2:
5'-TGTAGGCTGGAGCTGCTTCG3'

The H fragments were variable and specific
for the deletion of a given gene:
trkA deletion:
H1:
5'-TAATAAGGCGTCATTAGACGCCTTATTAATTACAAGAAGAAAGGGCT

TGG-3'

H2:
5'-TTTACGCTAAGCTAATCAAAAAGTGATGAGATAACGGGTCGCGACTG

ATG-3' kdpABC deletion:
H1:
5'-GACTCATATTCAGTGCTCACTCAATATCATCAGGAGAGATATTCCGC

CAC-3'

H2:
5'-GTCATTGATTTACTGCTGACCGTTTGCGGTCTGGTGTGAGGTTTACC

ATG-3' kup deletion:
H1:
5'-CCCCTTATGAAGAAAGGAGGCGTCTGGCGTTAGATTTCGACCTGAGT

ACC-3'

H2:
5'-GCCAAGGGACTAAGCACACATTTCATATTTCAACGAAAGACTAGTCT

ATG-3' mscS deletion:
H1:
5'-CAGAGAGTATTATCTGGCCTCAGCGTTGATTACGCAGCTTTGTCTTC

TTT-3'

H2:
5'-GGCGGAGTGTATTTCTCCATTTTGAGTCAGTTGAAAAGGAATATTGA

ATG-3' mscL deletion:
H1:
5'-ACCACTGGTCTTCTGCTTTCAGGCGCTTGTTAAGAGCGGTTATTCTG

CTC-3'

H2:
5'-TTAACATTTGTTAGACTTATGGTTGTCGGCTTCATAGGGAGAATAAC

ATG-3'
```

The PCR products were transformed via electroporation into the wild-type strain MG1655 (ATCC, No. 47076) of E. coli bearing the plasmid pKD46. The transformation was performed over 1 hour at 37° C. in SOC medium. The transformants were selected on KLM solid medium with kanamycine (25 μg/ml) at 37° C. Next, the transformants were passaged on LB without antibiotics and cultured at 43° C. The cells were tested for ampicillin sensitivity (loss of plasmid pKD46). Clones sensitive to ampicillin were then transformed with the plasmid pCP20. Transformants were selected on KLM medium with ampicillin (100 μg/ml) at 30° C., and then passaged on KLM without antibiotics at 43° C. Next, the individual colonies of E. coli were tested on KLM with ampicillin or kanamycin in order to confirm the loss of both antibiotic markers.

The resulting strains: E. coli (ΔKtrans), E. coli (ΔKtrans ΔmscL), E. coli (ΔKtrans ΔmscS) and E. coli (ΔKtrans ΔmscL ΔmscS) were tested for growth in various concentrations of potassium: non-limiting on media with a potassium concentration of 115 mM ($K_{115}$), as well as limiting with a potassium concentration of 1 and 15 mM ($K_1$, $K_{15}$). All of the abovementioned strains grew only on $K_{115}$ medium and failed to grow on $K_1$ and $K_{15}$.

EXAMPLE 2

Assay Identifying Potential Antibacterial Compounds

Media: The non-limiting medium for the growth of E. coli (ΔKtrans) mutants was $K_{115}$ containing $K_2HPO_4$, 46 mM; $KH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (Li et al., 2007). In order to obtain potassium-free medium, $K_0$, we used $Na_2HPO_4$, 46 mM; $NaH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (mass/volume). In order to prepare a medium with a median potassium content, we mixed $K_{115}$ and $K_0$ media in appropriate proportions.

The following bacterial strains: E. coli (ΔKtrans), E. coli (ΔKtrans ΔmscL), E. coli (ΔKtrans ΔmscS) and E. coli (ΔKtrans ΔmscL ΔmscS) were cultured on $K_{115}$ overnight. Next day, the bacteria of each strain were diluted to $OD_{600}$ ~0.01 in $K_1$, $K_5$, $K_{10}$, and $K_{15}$ media. The diluted cultures were aliquoted in batches of 100 μl into microtitration plates (96-well). These aliquots were supplemented with low molecular weight compounds at concentrations from 1 to 1000 nM. The cultures in the microtitration plates were incubated overnight at 37° C. with slight agitation (70 RPM). Growth of bacteria in individual wells was evaluated visually or using a SpectraMax plate reader (Molecular Devices) at a wavelength of 600 nm.

EXAMPLE 3

A Kit for Testing Compounds as Potential Substances with Antibacterial Activity

A kit for testing compounds as potential substances with antibacterial activity contains bacterial strains E. coli (ΔKtrans), E. coli (ΔKtrans ΔmscL), E. coli (ΔKtrans ΔmscS) and E. coli (ΔKtrans ΔmscL ΔmscS), as the non-limiting medium to the growth of E. coli (ΔKtrans) it contains $K_{115}$ containing $K_2HPO_4$, 46 mM; $KH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (Li et al., 2007), as well as a medium devoid of potassium ion, $K_0$, containing $Na_2HPO_4$, 46 mM; $NaH_2PO_4$, 23 mM; $(NH_4)_2SO_4$, 8 mM; $MgSO_4$, 0.4 mM; $FeSO_4$, 6 μM; sodium citrate, 1 mM; thiamine hydrochloride, 1 mg/l; and glucose, 0.2% (mass/volume).

The invention claimed is:

1. A mutant strain of *Escherichia coli*, possessing the deletion ΔKtrans of the following potassium transporter genes: Kdp, Kup and Trk, and further possessing the deletion ΔmscS and/or the deletion ΔmscL of at least one of the mechanically gated channel genes selected from the group consisting of mscS and mscL.

2. The mutant strain according to claim 1, possessing the following deletions: ΔKtrans and ΔmscS.

3. The mutant strain according to claim 1, possessing the following deletions: ΔKtrans and ΔmscL.

4. The mutant strain according to claim 1, possessing the following deletions: ΔKtrans, ΔmscS and ΔmscL.

5. A method of testing chemical compounds for potential antibacterial activity, comprising
producing a mutant of an *Escherichia coli* strain that possesses ΔKtrans deletions of the following potassium transporter genes: Kdp, Kup and Trk, measuring the growth of cultures of the resulting mutant *Escherichia coli* strain in the presence of the compound being tested and limiting potassium concentrations, wherein the growth of the *Escherichia coli* strain possessing the ΔKtrans deletions indicates the facilitation of potassium transport into the *Escherichia coli* cell by the tested compound, further comprising the following stages
producing a mutant *Escherichia coli* strain possessing ΔKtrans deletions of the following potassium transporter genes: Kdp, Kup and Trk as well as additionally possessing the deletion ΔmscS and/or the deletion ΔmscL of at least one of the genes encoding mechanically gated channels selected from the group consisting of mscS and mscL, using the same initial *Escherichia coli* strain, and then measuring the growth of this mutant in the presence of the tested compound and limiting concentrations of potassium, wherein:
the growth of a strain possessing ΔKtrans deletions and the growth of a strain possessing the deletions ΔKtrans, ΔmscS and ΔmscL indicates that the tested compound exhibits no activity towards the MscS and MscL channel proteins,
the growth of strains possessing ΔKtrans deletions, and the failure to grow of strains possessing the deletions ΔKtrans, ΔmscS and ΔmscL indicates the effect of the tested substance on mechanically gated receptors,
the growth of the strain possessing the deletions ΔKtrans and ΔmscL in the presence of the tested compound exhibiting an effect on the activity of mechanically gated channels indicates that the tested substance is a specific activator of the MscS channel,
the growth of the strain possessing the deletions ΔKtrans and ΔmscS in the presence of the tested compound exhibiting an effect on the activity of mechanically gated channels means that the tested compound is a specific activator of the MscL channel.

6. A kit for testing chemical compounds as potential antibacterial substances, containing the mutant strain of *Escherichia coli* of claim 1.

7. The mutant strain of *Escherichia coli* of claim 1, is a mutant of the strain *Escherichia coli* MG61655 (ATCC No. 47076).

8. The method of claim 5, wherein the *Escherichia coli* strain is a mutant of the strain *Escherichia coli* MG61655 (ATCC No. 47076).

\* \* \* \* \*